(12) United States Patent
Hirano

(10) Patent No.: US 10,231,631 B2
(45) Date of Patent: Mar. 19, 2019

(54) MEASUREMENT DEVICE AND MEASUREMENT METHOD

(71) Applicant: KYOCERA Corporation, Kyoto (JP)

(72) Inventor: Asao Hirano, Koganei (JP)

(73) Assignee: KYOCERA Corporation, Kyoto (JP)

(*) Notice: Subject to any disclaimer, the term of this patent is extended or adjusted under 35 U.S.C. 154(b) by 242 days.

(21) Appl. No.: 15/311,158

(22) PCT Filed: May 28, 2015

(86) PCT No.: PCT/JP2015/002707
§ 371 (c)(1),
(2) Date: Nov. 14, 2016

(87) PCT Pub. No.: WO2015/182149
PCT Pub. Date: Dec. 3, 2015

(65) Prior Publication Data
US 2017/0095165 A1 Apr. 6, 2017

(30) Foreign Application Priority Data

May 28, 2014 (JP) ................................. 2014-110248

(51) Int. Cl.
*A61B 5/0245* (2006.01)
*A61B 5/024* (2006.01)
(Continued)

(52) U.S. Cl.
CPC ........ *A61B 5/02416* (2013.01); *A61B 5/0245* (2013.01); *A61B 5/6815* (2013.01);
(Continued)

(58) Field of Classification Search
CPC ............ A61B 5/02416; A61B 5/02427; A61B 5/02433; A61B 5/02438; A61B 5/02444;
(Continued)

(56) References Cited

U.S. PATENT DOCUMENTS 6,808,473 B2 * 10/2004 Hisano ............... A63B 71/0686
482/8
2007/0127756 A1 6/2007 Slabaugh et al.
(Continued)

FOREIGN PATENT DOCUMENTS

JP H07-241279 A 9/1995
JP H11-070087 A 3/1999
(Continued)

OTHER PUBLICATIONS

An Office Action issued by the Japanese Patent Office dated Feb. 14, 2017, which corresponds to Japanese Patent Application No. 2014-110248 and is related to U.S. Appl. No. 15/311,158; with English language concise explanation.
(Continued)

*Primary Examiner* — Meredith Weare
(74) *Attorney, Agent, or Firm* — Studebaker & Brackett PC

(57) ABSTRACT

A measurement device includes an ear canal connection configured to be inserted into an ear canal, a shaft extending from the ear canal connection along an insertion direction, a biological sensor configured to be turnable about the shaft relative to the ear canal connection and a controller configured to measure the biological information based on a biometric output obtained from the biological sensor.

6 Claims, 5 Drawing Sheets

(51) Int. Cl.
*A61B 5/00* (2006.01)
*H04R 1/02* (2006.01)
*H04R 1/10* (2006.01)

(52) U.S. Cl.
CPC .......... *A61B 5/6817* (2013.01); *A61B 5/7221* (2013.01); *A61B 5/742* (2013.01); *H04R 1/028* (2013.01); *H04R 1/1016* (2013.01); *A61B 5/6803* (2013.01); *A61B 5/6898* (2013.01); *A61B 2562/16* (2013.01); *H04R 1/1041* (2013.01)

(58) Field of Classification Search
CPC .... A61B 5/0245; A61B 5/0255; A61B 5/6817
See application file for complete search history.

(56) References Cited

U.S. PATENT DOCUMENTS

| | | |
|---|---|---|
| 2008/0091113 A1 | 4/2008 | Kondo et al. |
| 2008/0220535 A1 | 9/2008 | Leboeuf et al. |
| 2009/0010461 A1* | 1/2009 | Klinghult ............ A61B 5/0002 381/309 |
| 2009/0069645 A1* | 3/2009 | Nielsen ................ A61B 5/02 600/301 |
| 2009/0177097 A1* | 7/2009 | Ma .................... A63B 71/0686 600/500 |
| 2011/0081037 A1 | 4/2011 | Oh et al. |
| 2012/0283578 A1 | 11/2012 | Leboeuf et al. |
| 2013/0296685 A1* | 11/2013 | Tsuboi ................ A61B 5/01 600/407 |
| 2013/0303923 A1* | 11/2013 | Lerner ............... A61B 5/02208 600/492 |
| 2014/0152970 A1 | 6/2014 | Wada et al. |

FOREIGN PATENT DOCUMENTS

| | | |
|---|---|---|
| JP | H11-113861 A | 4/1999 |
| JP | 2006-288636 A | 10/2006 |
| JP | 2007-167375 A | 7/2007 |
| JP | 2010-075761 A | 4/2010 |
| JP | 2012-050711 A | 3/2012 |
| JP | 2012-157423 A | 8/2012 |
| JP | 2013-031608 A | 2/2013 |
| WO | 2009/001449 A1 | 12/2008 |

OTHER PUBLICATIONS

International Search Report issued in PCT/JP2015/002707; dated Aug. 18, 2015.

Written Opinion issued in PCT/JP2015/002707; dated Aug. 18, 2015; with English language Concise Explanation.

* cited by examiner

MEASUREMENT DEVICE AND MEASUREMENT METHOD

CROSS-REFERENCE TO RELATED APPLICATION

This application claims priority to and the benefit of Japanese Patent Application No. 2014-110248 (filed on May 28, 2014), the entire contents of which are incorporated herein by reference.

TECHNICAL FIELD

This disclosure relates to a measurement device and a measurement method.

BACKGROUND

A biological information measurement device that measures the biological information, such as pulses or the like, of the user has been known. The biological information is measured by various methods by using a biological information measurement device.

SUMMARY

According to one embodiment of the present disclosure, a measurement device includes, an ear canal connection, a shaft a biological sensor and a controller. The ear canal connection is configured to be inserted into an ear canal. The shaft is extending from the ear canal connection along an insertion direction. The biological sensor is configured to be turnable about the shaft relative to the ear canal connection. The controller is configured to measure biological information based on a biometric output obtained from the biological sensor.

As described above, although a solution of this disclosure has been explained as devices, this disclosure can be realized as methods substantially corresponding to the devices, and it will be appreciated that the scope of this disclosure includes them.

For example, a measurement method according to this disclosure is a measurement method by a measurement device that includes a biological sensor configured to be turnable about a shaft extending from an ear canal connection along an insertion direction relative to the ear canal connection. The method includes a notification step in which, when a biometric output obtained from the biological sensor is not within an allowable range that can be used for measurement of biological information, a notification indicating that the biological sensor is needed to be turned is provided.

DETAILED DESCRIPTION

In the pulse measurement device, the measurement accuracy varies depending on the positional relationship between the pulse wave sensor and the blood vessel located on a measurement point of the pulse wave. However, in the conventional pulse measurement device, in some cases, the biological information could not be measured accurately for a difficulty in adjusting the position of the pulse wave sensor.

The present embodiment has been conceived in light of the above considerations and provides a measurement device and a measurement method capable of improving the measurement accuracy of the biological information.

The following describes embodiments of this disclosure with reference to the drawings.

Figure 1:
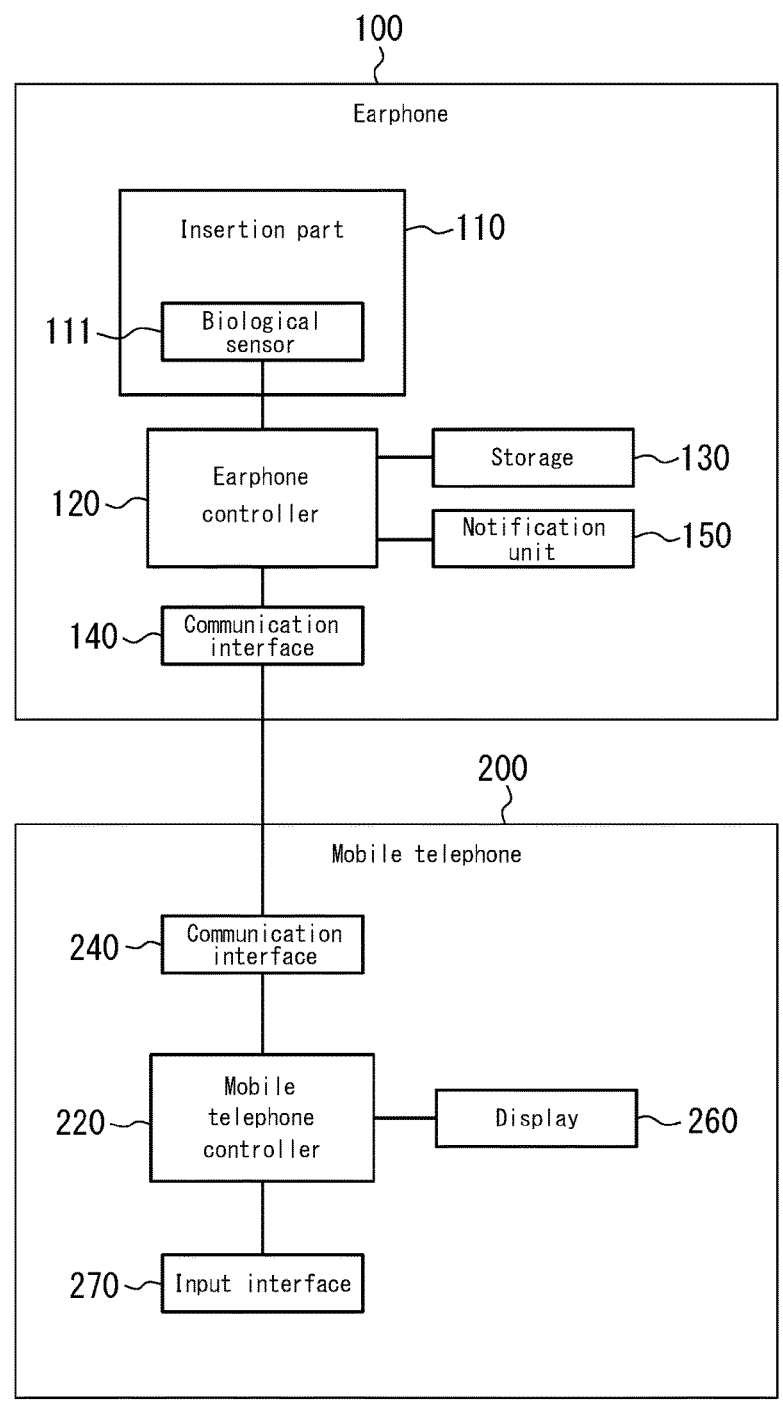
FIG. 1 is a functional block diagram of a measurement device according to one embodiment of this disclosure.

FIG. 1 is a functional block diagram of main parts of the measurement device according to one embodiment of this disclosure. The measurement device according to this disclosure is realized by an earphone 100. The earphone 100 includes an insertion part 110, an earphone controller 120, a storage 130, a communication interface 140 and a notification unit 150. The earphone 100 measures the biological information by using a biological sensor 111 mounted on the insertion part 110 with the insertion part 110 inserted to an ear canal of the user. When the earphone 100 according to this embodiment is used, the user may adjust the position of the biological sensor 111 beforehand. After adjusting the position once, the user does not need to adjust the position again unless the position of the biological sensor 111 is changed, for example.

The biological information is any information that can be measured by using the biological sensor 111 provided in the insertion part 110. As one example, the following explanation is given assuming that the earphone 100 measures the pulse of the user in this embodiment.

Figure 2:
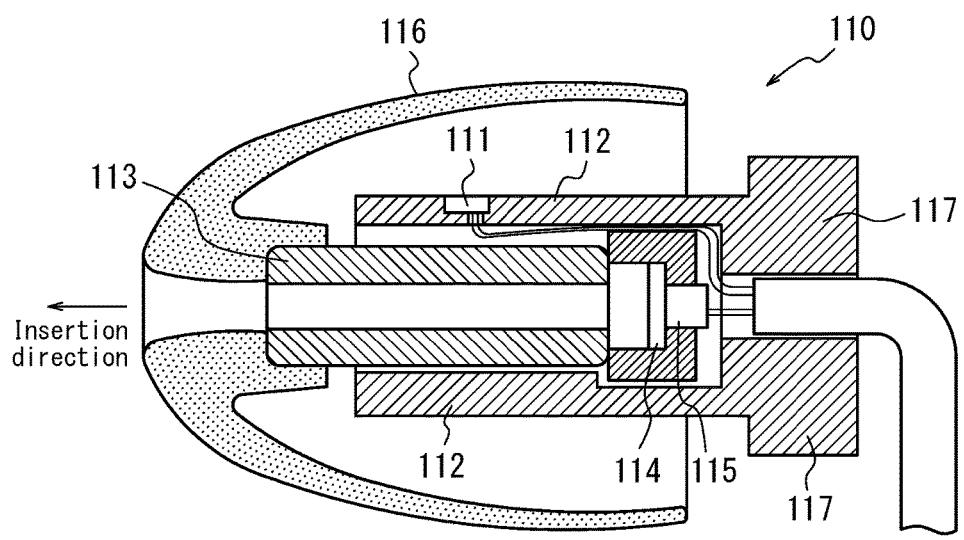
FIG. 2 is a diagram illustrating a cross-sectional schematic configuration of an insertion part according to one embodiment of this disclosure.

When the user measures pulse, he/she wears the insertion part 110 in his/her ear. FIG. 2 is a diagram illustrating a cross-sectional schematic configuration of the insertion part 110 according to one embodiment of this disclosure. In FIG. 2, the insertion part 110 is inserted into the user's ear canal to the left. The insertion part 110 includes the biological sensor 111, a sensor disposing part 112, a sound guide tube 113 as a shaft, a vibration plate 114, a driving unit 115 and an ear canal connection 116.

The biological sensor 111 is a pulse wave sensor and obtains pulse wave data, as a biometric output, from the user (living body). The biological sensor 111 includes a light-emitting element such as a LED (Light emitting diode) or the like and a light-receiving element such as a PT (Phototransistor) or a PD (Photodiode) or the like, for example. The biological sensor 111 measures the pulse wave data by allowing the light-emitting element to irradiate the measuring light to a region to be tested in an ear canal of the user and allowing the light-receiving element to receive the reflected light from the region to be tested. In the case of such measurement by the light, the biological sensor 111 does not always have to be in contact with the ear canal.

The biological sensor 111 is disposed on the outer periphery of the cylindrical sensor disposing part 112. In the earphone 100 according to this embodiment, the sensor disposing part 112 is disposed on the outer periphery side of the sound guide tube 113. The sensor disposing part 112 has a turn adjusting part 117 on the opposite side of the side inserting to the ear canal.

Figure 3:
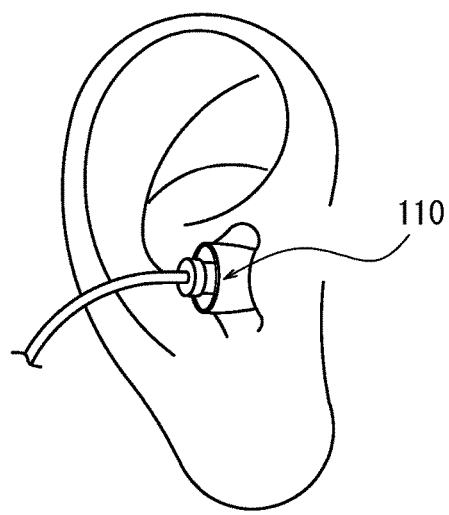
FIG. 3 is a diagram illustrating a state where the insertion part in FIG. 2 is inserted into an ear canal.

A part of the sensor disposing part 112 except for the turn adjusting part 117 is covered with the ear canal connection 116. The sensor disposing part 112 is configured to be turnable about the sound guide tube 113 relative to the sound guide tube 113 and the ear canal connection 116. The sensor disposing part 112 may be configured to be turnable clockwise/counterclockwise 180 degrees, respectively. The sensor disposing part 112 may include a lock mechanism with respect to each predetermined rotating angle (e.g. 10 degrees) and be configured to be turnable in stages. As illustrated in FIG. 3, for example, the user may pinch the turn adjusting part 117 with his/her fingers to turn it with the insertion part 110 inserted into his/her ear canal, thereby allowing the sensor disposing part 112 to be turned. As a result of this, the position of the biological sensor 111 disposed on the sensor disposing part 112 is changed. Thus, the region to be tested to which the biological sensor 111 irradiates the measuring light in the ear canal is changed. The user adjusts the position of the biological sensor 111 by turning the biological sensor 111.

The sound guide tube 113 is cylindrical and extends along the direction inserting to the ear canal. The sound guide tube 113 serves as a rotating shaft when the sensor disposing part 112 turns relative to the ear canal connection 116. The sound guide tube 113 transmits the sound generated by the sound generator (speaker unit) configured with the vibration plate 114 and the driving unit 115 in the insertion direction of the ear canal connection 116 to the ear canal, that is, transmits the sound into the ear of the user. The driving unit 115 causes the vibration plate 114 to vibrate based on a sound signal of the sound generated by a mobile telephone 200 as a sound source device. The vibration plate 114 vibrates based on the driving of the driving unit 115 to reproduce sound. Driving of the driving unit 115 is controlled by the earphone controller 120, for example.

The ear canal connection 116 covers a part of the insertion part 110 and contacts the ear canal when the insertion part 110 is inserted into the ear canal. The ear canal connection 116 is formed from a material that allows the measuring light irradiated from the biological sensor 111 and the reflected light from the region to be tested to transmit easily. For example, when the measuring light and the reflected light are infrared rays, the ear canal connection 116 may be formed from silicon.

With reference to FIG. 1 again, the earphone controller 120 is a processor that controls overall operation of the earphone 100. When the user measures the biological information, the earphone controller 120 measures pulse as the biological information based on the pulse wave data obtained from the biological sensor 111.

When the user adjusts the position of the biological sensor 111, the earphone controller 120 performs a predetermined control. For example, the earphone controller 120 determines whether or not the pulse wave data, which is the biometric output, is within the allowable range that can be used for measurement of the biological information. When the earphone controller 120 determines that the pulse wave data is not within the allowable range, it allows the notification unit 150 to indicate that the biological sensor 111 is needed to be turned. On the other hand, when the earphone controller 120 determines that the pulse wave data is within the allowable range, it adjusts the intensity of the measuring light irradiated from the biological sensor 111 to the region to be tested. The predetermined control performed by the earphone controller 120 when the user adjusts the position of the biological sensor 111 will be described in detail below with reference to FIG. 4.

The storage 130 can be configured with a semiconductor memory, a magnetic memory or the like, for example, and stores various kinds of information and a program for operating the earphone 100, or the like. The storage 130 stores the information (threshold) relating to the allowable range that is a criterion for determining whether or not the pulse wave data obtained by the biological sensor 111 can be used for the measurement of the biological information.

The communication interface 140 is connected to the sound source device wired or wirelessly by Bluetooth® or the like to communicate with each other. The sound source device can be any one of miscellaneous sound source devices such as, for example, a mobile telephone, a mobile music player, a laptop computer, a tablet terminator, a game machine, or the like. In this specification, explanation is give on the assumption that the sound source device is a mobile telephone 200. The earphone 100 transmits the biological information measured by the earphone controller 120, for example, to the mobile telephone 200 via the communication interface 140. The earphone 100 receives the information relating to a sound signal of the sound reproduced from the mobile telephone 200, for example, via the communication interface 140.

The notification unit 150 notifies the user that the biological sensor 111 is needed to be turned, based on the control by the earphone controller 120, by a visual method with images, characters, light emission or the like, an auditory method such as sound or the like, or a combination thereof. In the case of notification by an auditory method, the notification unit 150 provides a notification by displaying images or characters on a display device configured with a liquid crystal display, an organic EL display, an inorganic EL display or the like, for example. The notification unit 150 may notify by light emission of a light-emitting element such as a LED or the like that is configured separately from the biological sensor 111, for example. In the case of notification by an auditory method, the notification unit 150 provides a notification by outputting alarm sound, sound guide, or the like, from the sound generator provided in the insertion part 110, for example. It should be noted that the notification provided by the notification unit 150 is not limited to an auditory or visual notification, and the notification may be provided in any method that can be recognized by the user.

It should be noted that the earphone controller 120 may provide a notification by displaying images or characteristics on a display 260 of the mobile telephone 200 connected via the communication interface 140, for example. In this case, the earphone 100 does not need to include the notification unit 150.

The mobile telephone 200 can be a smartphone, for example, and is connected to the earphone 100. The mobile telephone 200 includes a mobile telephone controller 220, a communication interface 240, a display 260 and an input interface 270.

The mobile telephone controller 220 is a processor that controls overall operation of the mobile telephone 200. The mobile telephone controller 220 allows the display 260 to display the biological information measured by the earphone 100, for example. The mobile telephone controller 220 generates a sound signal of the sound reproduced from the insertion part 110 of the earphone 100, for example.

The communication interface 240 is connected wired or wirelessly to the earphone 100 to communicate with each other. The mobile telephone 200 receives the biological information measured by the earphone 100 via the communication interface 240, for example. The mobile telephone 200 transmits the information relating to the sound signal of the sound reproduced from the insertion part 110 of the earphone 100 to the earphone 100 via the communication interface 240, for example.

The display 260 is a display device such as, for example, a liquid crystal display, an organic EL display, an inorganic EL display, or the like. The display 260 displays the biological information measured by the earphone 100. The user can know his/her own biological information by confirming the display on the display 260.

The input interface 270 accepts an operation input from the user, and is configured with operation buttons (operation keys), for example. The input interface 270 may be configured with a touch screen, and an input region that accepts an operation input from the user may be displayed on a portion of the display 260 so that a touch operation input by the user can be accepted.

Figure 4:
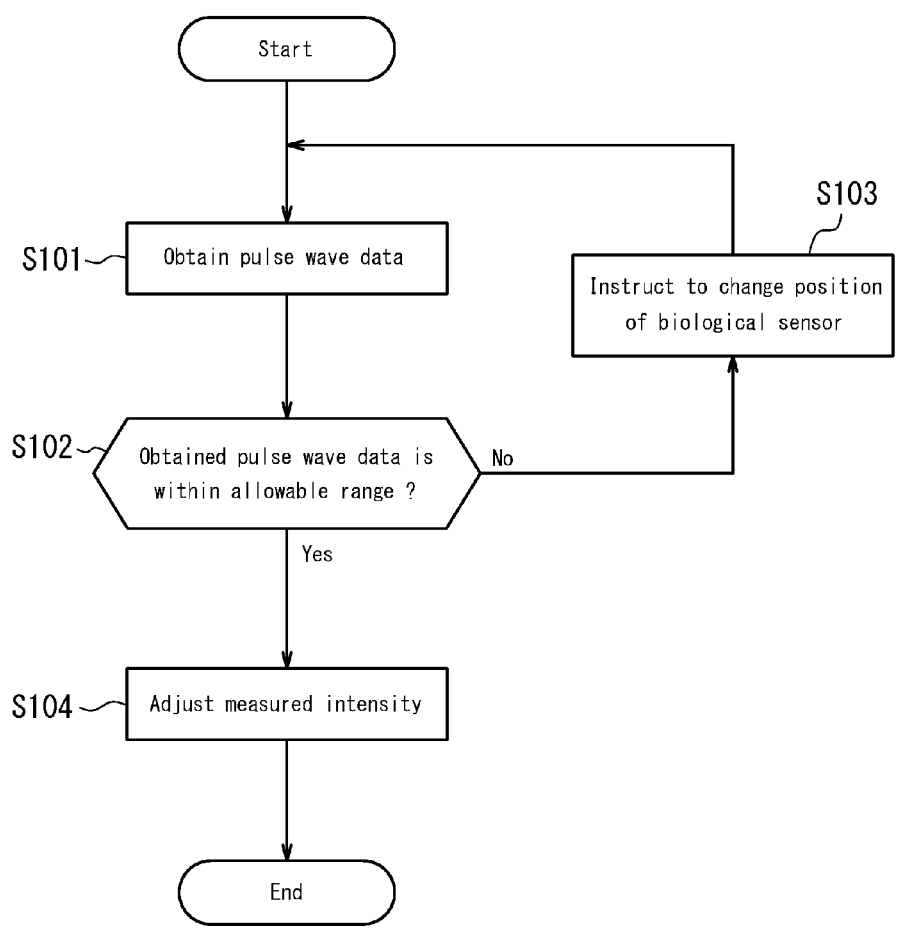
FIG. 4 is a flow chart illustrating an example of a process performed by an earphone controller illustrated in FIG. 1.

Next, the control performed by the earphone controller 120 when the user adjusts the position of the biological sensor 111 is described in detail below. FIG. 4 is a flowchart illustrating one example of a process performed by the earphone controller 120 illustrated in FIG. 1 when it adjusts the position. When the user measures the biological information by using the earphone 100 according to this embodiment, he/she adjusts the position of the biological sensor 111 beforehand. When the user adjusts the position, he/she performs a predetermined input to the input interface 270 of the mobile telephone 200, for example, to allow the earphone controller 120 to start the flow illustrated in FIG. 4.

First, the earphone controller 120 obtains the pulse wave data by using the biological sensor 111 (step S101). In particular, the earphone controller 120 obtains the pulse wave data by allowing the biological sensor 111 to irradiate the measuring light to the region to be tested and receive the reflected light from the region to be tested. At this time, the intensity of the measuring light to be irradiated is any intensity that allows the earphone controller 120 to determine whether the position of the biological sensor 111 should be changed or not. The intensity of this measuring light may be constant and may not change each time the flow in FIG. 4 is executed.

The earphone controller 120 determines whether or not the obtained pulse wave data is within the allowable range that can be used for measurement of the biological information (step S102).

Here, the method performed by the earphone controller 120 to determine whether or not the pulse wave data is within the allowable range is described in detail. The earphone controller 120 determines whether or not the obtained pulse wave data is within the allowable range according to the threshold relating to the allowable range stored in the storage 130. The threshold relating to the allowable range is, for example, a threshold relating to the number of peaks in a predetermined period of time, for example, and the earphone controller 120 determines whether or not the pulse wave data is within the allowable range based on whether or not the number of peaks of the pulse wave data is within the range of the threshold.

Figure 5A:
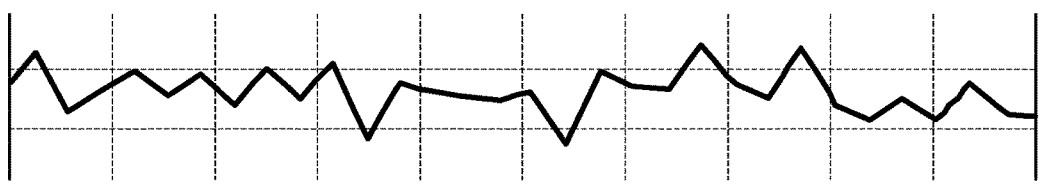
FIG. 5A and FIG. 5B are a diagram illustrating one example of the pulse wave data obtained by a biological sensor illustrated in FIG. 1.
Figure 5B:

FIG. 5A and FIG. 5B are a diagram illustrating an example of the pulse wave data obtained by the biological sensor 111 illustrated in FIG. 1. When comparing FIG. 5A and FIG. 5B, the number of peaks of the pulse wave data in FIG. 5A is greater than that of the pulse wave data in FIG. 5B. For example, when the number of peaks of the pulse wave data in FIG. 5A is out of the range of the threshold stored in the storage 130, the earphone controller 120 determines that the pulse wave data includes a lot of noise and the pulse wave data is not within the allowable range. On the other hand, when the number of peaks of the pulse wave data in FIG. 5B is within the range of the threshold stored in the storage 130, for example, the earphone controller 120 determines that the pulse wave data is within the allowable range.

It should be noted that the threshold relating to the allowable range is not limited to this example. The threshold relating to the allowable range can be any threshold that allows the earphone controller 120 to determine whether or not the pulse wave data is within the allowable range. For example, the threshold can be those relating to variation in the heights of peaks of the pulse wave data. The variation in the heights of peaks is defined by the standard deviation, for example. In this case, when the standard deviation of the height of peak is larger than the predetermined threshold, the earphone controller 120 determines that the pulse wave data has a lot of noise and the pulse wave data is not within the allowable range. On the other hand, in the case where the variation in the heights of peaks is smaller than the predetermined threshold, the earphone controller 120 determines that the pulse wave data is within the allowable range.

With reference to FIG. 4 again, in step S102, when the earphone controller 120 determines that the obtained pulse wave data is not within the allowable range (No in step S102), it displays an instruction to the user indicating that the position of the biological sensor 111 is needed to be changed (step S103). The earphone controller 120 can allow the notification unit 150 to notify the instruction indicating that the position of the biological sensor 111 is needed to be changed, for example. The earphone controller 120 can allow the display 260 of the mobile telephone 200 to display the instruction indicating that the position of the biological sensor 111 is needed to be changed, for example. Based on the instruction to change the position, the user changes the position of the biological sensor 111 by turning the turn adjusting part 117.

The earphone controller 120 uses the biological sensor 111 and obtains the pulse wave data again (step S101). At this time, the position of the biological sensor 111 has been changed based on the instruction of the earphone controller 120 in step S103, thus the region to be tested from which the biological sensor 111 obtains the pulse wave data has been changed. Since the pulse wave data varies depending on the positional relationship between the region to be tested and the biological sensor 111, it is assumed that the pulse wave data to be obtained by the earphone controller 120 is different from the pulse wave data that has been obtained earlier.

The earphone controller 120 determines whether or not the newly obtained pulse wave data is within the allowable range that can be used for measurement of the biological information (step S102).

When the earphone controller 120 determines that the obtained pulse wave data is not within the allowable range (No in step S102), it displays an instruction indicating that the position of the biological sensor 111 is needed to be changed again to the user (step S103). In this manner, the earphone controller 120 repeats steps S101 to S103 until it determines that the obtained pulse wave data is within the allowable range.

When the earphone controller 120 determines that the obtained pulse wave data is within the allowable range (Yes in step S102), it adjusts the measured intensity of the biometry information in the biological sensor 111 (step S104). For example, the earphone controller 120 adjusts the intensity of the measuring light outputted from the light-emitting element of the biological sensor 111. As a result of this, the earphone controller 120 can adjust the light receiving intensity of the reflected light in the pulse wave data obtained by the biological sensor 111 to the intensity suitable for measurement of the biological information. In this manner, the earphone controller 120 finishes control for adjusting the position of the biological sensor 111. After adjusting the position of the biological sensor 111, the user can measure the biological information.

It should be noted that, once adjusting the position of the biological sensor 111, for example, the user can repeatedly measure the biological information without adjusting the position again unless there is a change in the position of the biological sensor 111 in the insertion part 110, for example.

As explained above, in the earphone 100, the position of the biological sensor 111 is adjusted before the biological information of the user is measured. Since the biometric output obtained by the biological sensor 111 varies depending on the positional relationship between the biological sensor 111 and the region to be tested, in the earphone 100, the biological sensor 111 can be disposed on a position where the biological information can be measured with a high accuracy by adjusting the position before measuring the biological information. Thus, according to the earphone 100, the measurement accuracy of the biological information can be improved.

In the earphone 100, the user can change the position of the biological sensor 111 by pinching the turn adjusting part 117 with his/her fingers to turn it, and thus the user can adjust the position easily. Besides, even if the position of the biological sensor 111 is changed by the turn adjusting part 117, the ear canal connection 116 being in contact with the ear canal of the user does not move in the ear canal of the user, and as a result, the wearing feeling of the earphone 100 does not change.

As illustrated in FIG. 2, when the biological sensor 111 is disposed in the sensor disposing part 112 that is different from the sound guide tube 113 and the sensor disposing part 112 is disposed on the outer periphery side of the sound guide tube 113, the biological sensor 111 is less influenced by the vibration of the sound transmitted through the sound guide tube 113. That is, the biological sensor 111 is less vibrated by the vibration of sound. As a result, the biological sensor 111 can obtain the biometric output with a high accuracy.

It should be noted that this disclosure is not limited to the above described embodiment, and a variety of modifications or changes are possible. For example, the functions or the like included in each component, step or the like may be reordered in any logically consistent manner, and a plurality of components, steps or the like may be combined into one or divided.

For example, in the above described embodiment, the earphone controller 120 performs a predetermined control when the user adjusts the position of the biological sensor 111. However, the control is performed not only by the earphone controller 120. The control may be performed by the mobile telephone controller 220, for example.

Figure 6:
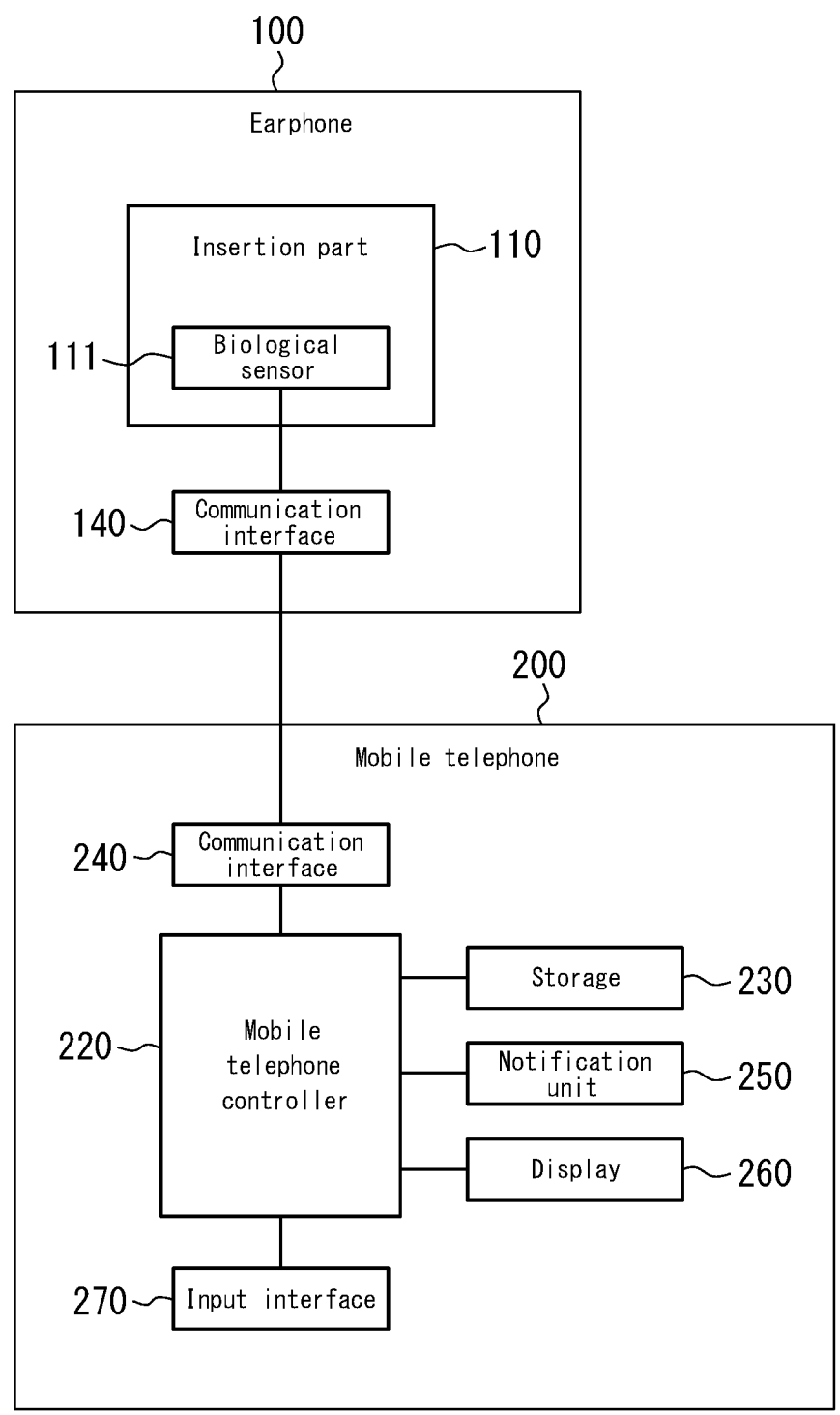
FIG. 6 is a functional block diagram of main parts of the measurement device in the case where a predetermined control for position adjustment is performed by a mobile phone controller 220.

FIG. 6 is a functional block diagram of main parts of the measurement device in the case where the mobile telephone controller 220 performs a predetermined control when the position is adjusted. In this case, the earphone 100 includes the insertion part 110 having the biological sensor 111 and the communication interface 140 that connects to the mobile telephone 200 wired or wirelessly to communicate with each other. The user operates the input interface 270 of the mobile telephone 200 and starts the application for measurement of the biological information, for example, to measure the biological information by using the earphone 100. The biological sensor 111 obtains the pulse wave data in the same manner as that of the above described embodiment. The communication interface 140 transmits the pulse wave data obtained by the biological sensor 111 to the mobile telephone 200.

When adjusting the position of the biological sensor 111, the user uses the position adjustment function of the above described application for measurement of the biological information. When the mobile telephone 200 obtains the pulse wave data from the earphone 100 via the communication interface 240, it performs a predetermined control to adjust the position in the mobile telephone controller 220. For example, the predetermined control is the control illustrated by the flow in FIG. 4. When performing the predetermined control, the mobile telephone controller 220 refers to the information relating to the allowable range that can be a criterion for determining whether the pulse wave data can be used or not for measurement of the biological information. The information relating to the allowable range is stored in the storage 230 of the mobile telephone 200, for example. When the mobile telephone controller 220 instructs to change the position of the biological sensor 111 in the step S103 in FIG. 4, it may instruct to change the position by providing a notification from the notification part 250 of the mobile telephone 200.

The user measures the biological information after the position of the biological sensor 111 is adjusted by controlling the mobile telephone controller 220. In this case, the pulse wave data obtained by the biological sensor 111 is transmitted from the earphone 100 to the mobile telephone 200 via the communication interface 140. In the mobile telephone 200, the mobile telephone controller 220 measures the biological information based on the obtained pulse wave data. The measurement results are displayed on the display 260 of the mobile telephone 200.

In the above described embodiment, although the insertion part 110 was explained as it includes the sensor disposing part 112 and the sound guide tube 113, the insertion part 110 is not limited to that described in this embodiment. The insertion part 110 may have any structure if the biological sensor 111 is configured to be turnable relative to the ear canal connection 116. For example, the insertion part 110 includes the sensor disposing part 112 in which the biological sensor 111 is disposed, and the sensor disposing part 112 may serve as a sound guide tube that transmits sound. That is, in this case, unlike the above described embodiment. the insertion part 110 includes only one cylindrical member. As a result of this, the insertion part 110 can be configured in more simplified structure.

In the insertion part 110, as a mechanism to apply electrical signals to the biological sensor 111 and the driving unit 115, a slip ring may be used.

The invention claimed is:

1. A measurement device, comprising:
an ear canal connection configured to be inserted into an ear canal;
a shaft extending from the ear canal connection along an insertion direction;

a biological sensor configured to be turnable about the shaft relative to the ear canal connection; and
a controller configured to measure biological information based on a biometric output obtained from the biological sensor.

2. The measurement device according to claim 1, further comprising:
a sensor disposing part configured to be turnable about the shaft relative to the ear canal connection, wherein
the biological sensor is disposed on an outer periphery of the sensor disposing part.

3. The measurement device according to claim 1, further comprising:
a sound generator; and
a sensor disposing part that is disposed on an outer peripheral side of the shaft and has the biological sensor disposed on the outer periphery, wherein
the shaft transmits sound generated by the sound generator; and
the sensor disposing part is turnable about the shaft relative to the ear canal connection.

4. The measurement device according to claim 1, wherein, when the biometric output is not within an allowable range that can be used for measurement of the biological information, the controller allows a notification unit to notify that the biological sensor is needed to be turned.

5. The measurement device according to claim 4, wherein, when the biometric output is within the allowable range, the controller adjusts a measured intensity of the biometric output in the biological sensor.

6. A measurement method by a measurement device comprising a biological sensor configured to be turnable about a shaft extending from an ear canal connection along an insertion direction relative to the ear canal connection,
the method comprising a notification step in which, when a biometric output obtained from the biological sensor is not within an allowable range that can be used for measurement of biological information, a notification indicating that the biological sensor is needed to be turned is provided.

* * * * *